United States Patent [19]

Drechsler

[11] Patent Number: 5,601,619
[45] Date of Patent: Feb. 11, 1997

[54] PHOTOTHERAPEUTIC DEVICE AND METHOD

[76] Inventor: Howard J. Drechsler, 26900 N. Woodland Rd., Beachwood, Ohio 44122

[21] Appl. No.: 166,092

[22] Filed: Dec. 13, 1993

[51] Int. Cl.⁶ ..................................................... A61N 5/06
[52] U.S. Cl. ............................................................. 607/88
[58] Field of Search ................................... 607/88–9, 94; 364/413.26, 413.01

[56] References Cited

U.S. PATENT DOCUMENTS 4,279,254  7/1981  Boschetti et al. ................ 607/94

FOREIGN PATENT DOCUMENTS

| | | | |
|---|---|---|---|
| 2937598 | 3/1981 | Germany | 607/88 |
| 2034462 | 6/1980 | United Kingdom | 607/88 |
| 2208803 | 4/1989 | United Kingdom | 607/88 |
| 9409850 | 5/1994 | United Kingdom | 607/88 |
| 9009812 | 9/1990 | WIPO | 607/88 |

*Primary Examiner*—Angela D. Sykes
*Attorney, Agent, or Firm*—Roger D. Emerson

[57] ABSTRACT

A microprocessor to control and to prevent failure in mechanisms, particularly those that perform timed intervals of work. The microprocessor controls the length of each interval of work, and limits the mechanism to perform only a predetermined number of work intervals, after which it deactivates the device, allowing the mechanism to reactivate only after entry of a coded number or operation of a key switch. The microprocessor monitors all functions of the mechanism and includes a first failsafe circuit that shuts down the mechanism in the event of malfunction. A second failsafe circuit monitors the first failsafe circuit, and bypasses it to shut down the mechanism in the event of malfunction in the first failsafe circuit.

7 Claims, 4 Drawing Sheets

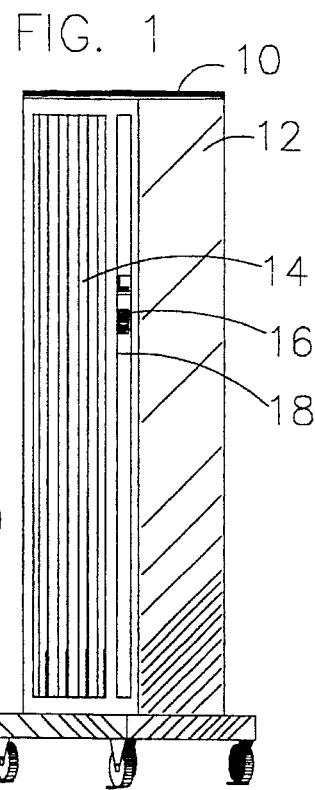
FIG. 1
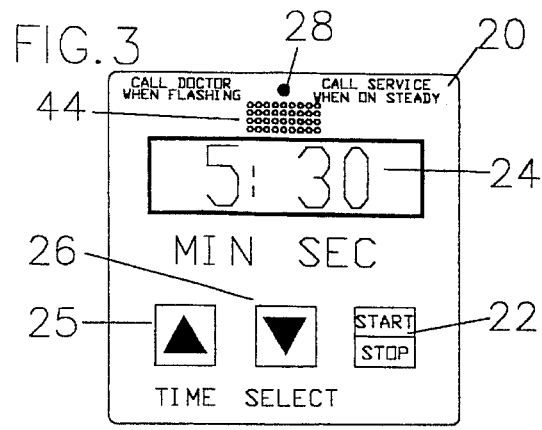
FIG. 3
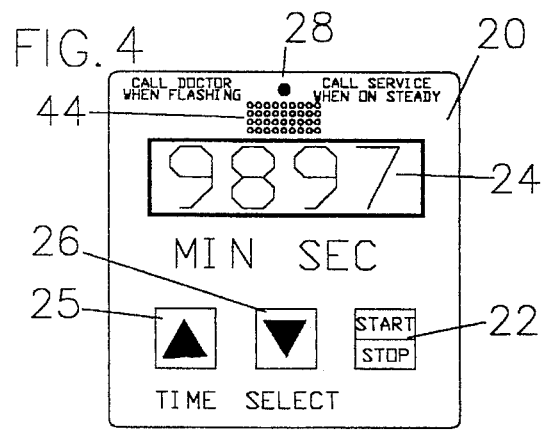
FIG. 4
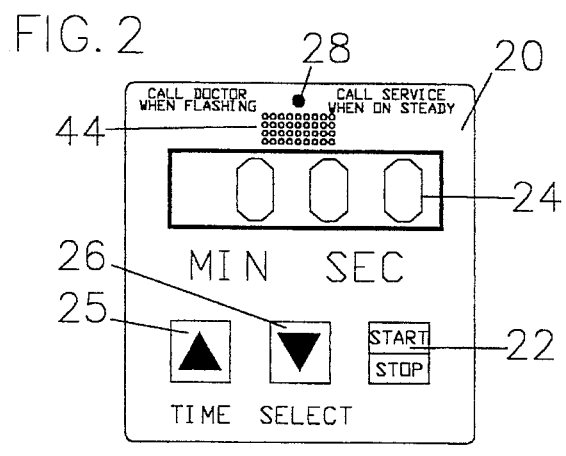
FIG. 2
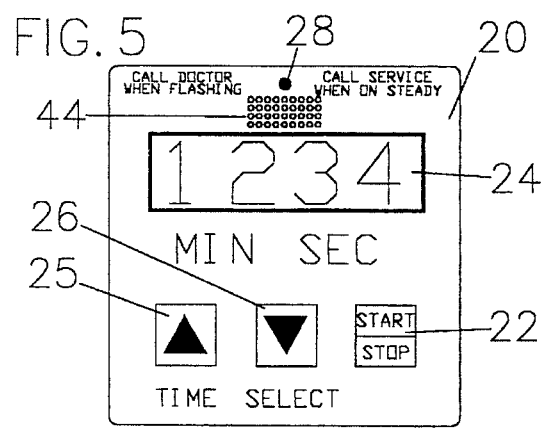
FIG. 5
FIG. 6
| DEACTIVATE CODE NUMBER | REACTIVATE CODE NUMBERS | | | | |
|---|---|---|---|---|---|
| | 25 TREATMENTS | 50 TREATMENTS | 100 TREATMENTS | 200 TREATMENTS | UNLIMITED TREATMENTS |
| 9897 | 1234 | 4321 | 3412 | 2143 | 3142 |

PHOTOTHERAPEUTIC DEVICE AND METHOD

BACKGROUND OF THE INVENTION

1. Field of Invention

The general field of invention relates to failsafe controls for mechanisms that perform repetitive cycles of work. More specifically, the field of invention relates to failsafe controls for mechanisms used in the health care industry, including diagnostic and therapeutic mechanisms programmable to dispense selectable timed events. Most specifically, the field of invention relates to phototherapeutic radiation devices for home use.

2. Description of Related Art

In the general field of commerce there are many examples of automatic mechanisms that intermittently perform work responsive to actuating means, timed or non-timed. Furnaces, air conditioners, ovens, kitchen appliances, lights, photocopy machines, and telecommunication devices are but a few examples of miscellaneous prior art apparatus to illustrate the diversity of mechanisms that will benefit from the subject invention. In the health care industry, the device is of particular benefit to photochemotherapeutic and phototherapeutic ultraviolet radiation devices, autoclaves, therapeutic and diagnostic X-ray machines, including CT-scans and fluoroscopes, ultrasound, magnetic resonance and other body-imaging devices.

SUMMARY OF THE INVENTION

The subject invention was developed to solve specific safety problems associated with the use of therapeutic ultraviolet radiation machinery by providing a system of treatment that can be safely administered in a patient's home, without personal technical supervision. A preferred embodiment of the invention comprises a prescription-controlled, patient-operated, medical phototherapy treatment dispensing device. Coded prescription numbers which are entered in a programmable microprocessor control the number and length of treatments. When the prescribed number of treatments have been dispensed, a microprocessor counter deactivates the device so that it is no longer operable by the patient. If the patient's physician wishes the treatments to continue, the physician provides the patient with a new coded prescription comprising a three or four-digit number. The patient scrolls this number code onto a microprocessor LED display, which reactivates the device for another series of treatments pursuant to the second coded prescription.

To protect the patient from overexposure to ultraviolet radiation, a special failsafe sensor monitors all functions of the microprocessor. Upon detection of a malfunction, the failsafe monitor deactivates the ultraviolet radiation means and activates audio and video warnings. In addition, failsafe circuitry monitors the sensor itself. Thus the inventive concept provides dual failsafe monitoring, wherein a first failsafe circuit monitors the operation of the machinery to which it applies, and a second failsafe circuit monitors the operation of the failsafe circuit itself.

The inventive concept is applicable to any mechanism that is intended to operate for a preset length of time, and then to turn off. In an X-ray machine, for instance, if the machine malfunctions and does not shut off after the preset time, the inventive failsafe circuit will shut off the machine. Also, if a machine is scheduled for calibration and/or preventative maintenance after a predetermined number of cycles, the inventive failsafe circuit will deactivate the machine in a manner that prevents reactivation unless certain procedures are followed. In kitchen equipment, e.g., ovens or deepfat fryers, a timer failure can result in a ruined product or a fire. The failsafe feature of the subject invention protects against such events. The invention is also useful in combination with machines that require maintenance inspections and/or repairs after a pre-determined period of operation, such as various types of motors and generators.

Accordingly, although the invention is described primarily in terms of therapeutic ultraviolet radiation machinery, it will be appreciated that the invention can benefit any mechanism which has the means to provide selected timed events, and can provide failsafe means to protect any mechanism from failure during operation or from excessive use.

OBJECTS OF THE INVENTION

It is, therefore, an object of the invention to provide a mechanism control means that will prevent the mechanism from failing in the on position.

It is another object of the invention to provide a mechanism control which will limit the operation of the mechanism to a predetermined length of time or to a predetermined number of events.

It is another object of the invention to provide a mechanism control means which will monitor all vital functions of the mechanism and emit audio and/or video warnings when it detects a malfunction of the mechanism.

It is another object of the invention to provide mechanism control means which will monitor all vital functions of the mechanism and which will shut the mechanism down when it detects a malfunction of the mechanism.

It is another object of the invention to provide a mechanism control means which will monitor all vital functions of the mechanism, and which includes failsafe means to monitor the control means.

It is another object of the invention to provide a mechanism control means with first failsafe means to monitor the control means and second failsafe means to monitor the first failsafe means.

It is another object of the invention to provide a mechanism control means which will control the length of a single operation of the mechanism, control the number of operations of the mechanism, and provide audio and/or video warnings and/or means to deactivate the mechanism when a malfunction occurs.

It is another object of the invention to provide ultraviolet radiation equipment for home use available only by physician's prescription.

It is another object of the invention to provide an ultraviolet radiation device that is programmed to dispense timed treatments to a patient and that will deactivate after it has dispensed a predetermined number of timed treatments.

It is yet another object of the invention to provide an ultraviolet radiation device with a programmable microprocessor having an LED digital display module into which coded numbers may be entered to generate command signals to the microprocessor to perform predetermined functions.

It is still another object of the invention to provide a microprocessor program to protect the user of the device from overexposure to ultraviolet radiation.

It is a further object of the invention to provide a device with failsafe means to monitor all functions of both the ultraviolet radiation device and the microprocessor and to deactivate the device when a malfunction is detected.

It is a still further object of the invention to provide a device that spaces dispensed treatments by predetermined time intervals.

BRIEF DESCRIPTION OF THE DRAWINGS

The foregoing and other objects and features of the invention will become apparent from the following description of preferred embodiments of the invention with reference to the accompanying drawings, in which:

FIG. 1 is a front elevational view in perspective of a preferred embodiment of the inventive device;

FIG. 2 is a front elevational view of the microprocessor programmer digital entry and LED display panel used in a preferred embodiment of the invention, showing the initial reading of zero, prior to programming for use;

FIG. 3 is a front elevational view of the digital entry and LED display panel of FIG. 2 showing an entered preselected time for one treatment;

FIG. 4 is a front elevational view of the digital entry and LED display panel of FIG. 2 showing an illustrative code number to be given to the physician by the patient for cross-referencing to a second coded number required to reprogram the device to dispense another limited number of treatments;

FIG. 5 is a front elevational view of the digital entry and LED display panel of FIG. 2 showing the programmed code number given by the physician to the patient in order to reprogram the device to dispense another limited number of treatments;

FIG. 6 is an illustrative display of coded numbers recorded in the physician's coded number logbook for use to practice the invention, as shown in FIGS. 4 and 5;

DETAILED DESCRIPTION OF A PREFERRED EMBODIMENT OF THE INVENTION

Ultraviolet Radiation Devices

Figure 7:
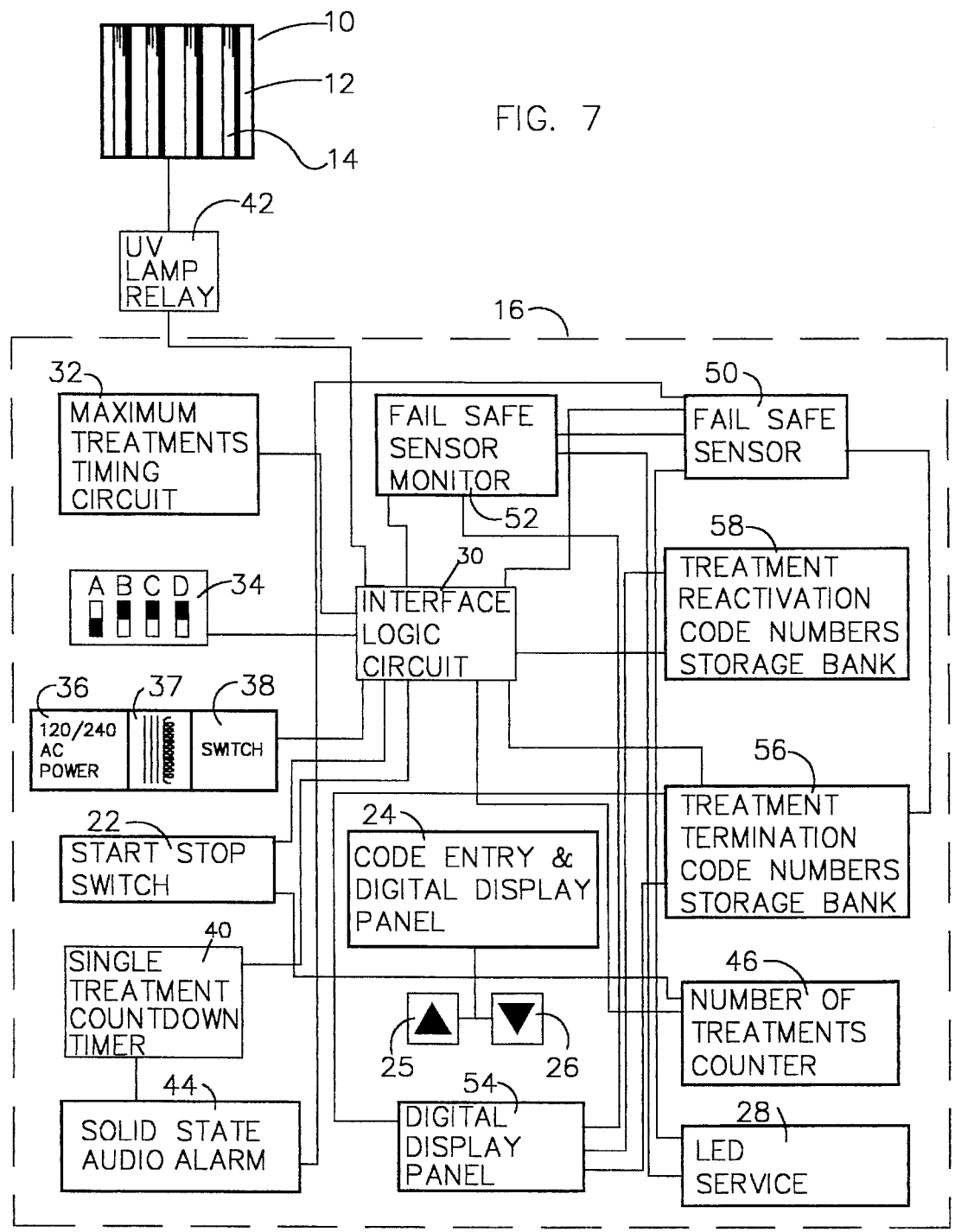
FIG. 7 is a schematic block diagram of a preferred embodiment of the invention.

Since the inventive therapeutic ultraviolet radiation treatment device is presently the most complex embodiment of the invention, for explanatory purposes it will be described as the first preferred embodiment. Referring first to FIG. 1, therein is shown the inventive device 10 comprising an ultraviolet radiation reflecting panel 12 containing a bank of ultraviolet ray-emitting tubes 14. This device 10, by FDA regulations, can be sold only by the manufacturer to a patient upon presentation of a prescription from a duly accredited physician. The physician prescribes the number of treatments of the initial regimen and the length of time of each treatment. Both the maximum number of treatments and the maximum duration of each treatment are preset into the device by the manufacturer according to the prescription. In a preferred embodiment of the invention, the device may be factory preset for a maximum number of treatments, e.g., twenty-five, fifty, one hundred, or two hundred, or the number may be unlimited in certain circumstances.

Although the duration of each treatment is preset in the preferred embodiment of the invention for a maximum length of ten, twenty, or thirty minutes, the patient may program treatments of shorter duration.

A programmable microprocessor 16 is mounted in the front face 18 of panel 12. As shown in FIG. 2, the microprocessor 16 is provided with a display panel 20 which includes a start/stop button 22, a digital entry and LED display screen 24, "up" button 25 which calls up and indexes digital numbers on the display screen 24 in sequentially increasing order, "down" button 26 to index digital numbers on the display screen 24 in sequentially decreasing order, and a combination warning LED light 28 and solid state audio alarm 44 to alert the patient to an operating condition of the device 10. Display screen 24 in FIG. 2 also displays three zeros to indicate that no single treatment time has yet been entered into the microprocessor 16.

Display screen 24 of FIG. 3 indicates that a single treatment time of five minutes and thirty seconds has been programmed into the microprocessor timer 16.

Display screen 24 of FIG. 4 displays one of the series of sequentially coded numbers that may appear on the display screen 24 when five or fewer treatments of the preset number of total treatments remain to be dispensed by the device 10. After the remaining five treatments have been dispensed, the microprocessor 16 deactivates the UV lamps 14. At this time, the patient consults with his physician, and the patient reads the numeral appearing on the display screen 24, e.g., 9897, FIG. 4, to the physician for cross reference to the physician's confidential coded number logbook. From the logbook the physician selects a predetermined reprogramming coded number for the additional number of treatments he will prescribe for this patient. If he decides, for example, that the patient should have an additional twenty-five treatments, he scans the column of sequentially listed coded numbers comprising the left-hand columns of the pages of the coded number logbook until he finds the numeral 9897. See FIG. 6. By reading across from left to right, he notes that to reprogram the device for an additional twenty-five treatments, the reprogramming coded number is 1234. The physician gives the coded number 1234 to the patient, who enters that number on the display screen 24, as shown in FIG. 5, by depressing the up button 25 until the screen displays the number 1234. With this new coded number displayed, the patient depresses the start/stop button 22. If the solid state alarm 44 sounds twice, the new coded number is either incorrect or was not properly entered. When the new coded number has been correctly derived and correctly entered, the solid state alarm 44 sounds once and the display indexes to 0:00 to indicate that treatments may resume.

Had the physician elected to prescribe fifty additional treatments, reference to the coded number logbook, FIG. 6, shows that the reprogramming coded number to be given to the patient is 4321. Although FIG. 6 shows only three representative lines from a physician's coded number logbook, in actual practice the inventive device may be programmed with over eight thousand deactivation coded numbers and over forty thousand corresponding reactivation code numbers, all of which are recorded in the physician's coded number logbook. The prolixity of code numbers prevents a patient from circumventing the physician's prescription and provides longevity for the coded number logbook and the memory banks of coded numbers programmed into the microprocessor. It should be noted that the coded numbers selected and discussed herein are for illustrative purposes only, and have been arbitrarily selected to protect the confidentiality of the physician's coded number logbook.

To begin treatment, the patient enters the prescribed length of treatment time, FIG. 3, and pushes the start/stop button 22, which energizes ultraviolet lamps 14. A single treatment countdown timer 40, FIG. 7, starts its countdown to zero, which is graphically shown on display screen 24, FIG. 3. The patient can determine at any time how many treatments remain to be dispensed by depressing the up button 25 and the down button 26 simultaneously.

Referring to FIG. 7 in greater detail, therein is shown in block diagram the ultraviolet ray dispenser panel 12 in combination with the microprocessor 16 which controls the ultraviolet ray emission. The interface microchip logic circuit 30 coordinates and controls all functions of the microprocessor 16. When the patient receives the device 10 from the manufacturer, it is preset for a selected number of treatments by maximum treatments timing circuit 32 and for a maximum duration of individual treatments with mechanical four-position dip switch 34. Dip switch 34 is not electronically programmable, but may be mechanically preset to any one of three time settings, ten, twenty, or thirty minutes. When switch 34A is closed, i.e., black in the down position, with switches 34B and 34C open, i.e., black in the up position, the maximum time selectable for the timer 40 is ten minutes. When switch 34B is closed, with switches 34A and 34C open, the maximum time selectable is twenty minutes. When switches 34A and 34B are open and switch 34C is closed, the maximum time selectable is thirty minutes. Switch 34D is independent of switches 34A, 34B, and 34C, and when closed will disable the maximum treatments timing circuit 32. The dip switch 34 is not accessible to the patient, and can be changed only by a factory technician upon the patient's presenting a timing modification prescription from the patient's physician to the manufacturer.

In order to place the device in use, a 120 or 240 AC power source 36 is connected to a 12 VAC stepdown transformer 37, which is connected through power switch 38 to the microprocessor logic circuit 30 and to start/stop switch 22. When the device is first powered, the digital display screen 24 defaults to zero, as shown in FIG. 2.

The patient may interrupt the countdown at any time by again pressing the start/stop button 22. The timer 40 stops, the countdown halts, as would be shown on the digital display screen 24, and UV lamp relay 42 opens and deenergizes ultraviolet lamps 14. To resume the treatment, the patient once more presses the start/stop button 22, UV lamp relay 42 closes and reenergizes ultraviolet lamps 14, and the countdown resumes, as again is shown on digital display screen 24. When the countdown reaches zero, the solid state alarm 44 sounds, and the countdown timer 40 opens the UV lamp relay 42 to deenergize the ultraviolet lamps 14.

Each time start/stop switch 22 initiates a treatment, including those treatments resumed after an interruption, the total number of prescribed treatments is reduced by one, as tracked by the treatment counter 46. When the number of remaining treatments have been counted down to five, an LED signal 28 flashes and the solid state alarm 44 sounds to alert the patient that a new prescription is required if treatments are to continue after the countdown reaches zero. When the counter 46 records zero as the number of remaining treatments, the UV lamp relay 42 again opens to deenergize lamps 14. At this juncture of operation, the patient is unable to reenergize lamps 14.

After the LED signal 28 flashes to signal that only five treatments remain to be dispensed, the next time the equipment is powered, the LED digital display screen 24 will show a three or four-digit code number, programmed into the treatment termination coded number storage bank 56, FIG. 7. See also FIG. 4. As aforesaid, the patient relays this number to the prescribing physician, who consults his coded number logbook to find the corresponding coded number programmed into the treatment reactivation coded number storage bank 58, FIG. 7, that will reactivate the system after the counter 46, FIG. 7, reaches zero.

Since one of the primary objects of the invention is to protect the patient under all conceivable circumstances from overexposure to ultraviolet radiation, failsafe sensor 50 continuously monitors all circuits, relays, and switches while the equipment is powered. In the event that failsafe sensor 50 detects a malfunction in the system, the service LED 28 emits a steady light. Malfunctions generally fall into two categories: failure of UV lamps 14 to turn off, and failure in electronic circuitry. When the UV lamps 14 fail to turn off upon conclusion of a treatment, failsafe sensor 50 signals logic circuit 30 to deactivate UV lamp relay 42, which turns off UV lamps 14. When there is a failure in the electronic circuitry, sensor 50 initiates a signal that results in the opening of the UV lamp relay switch 42, and solid state alarm 44 emits pulsating sounds continuously until the power 36 is removed from the system.

Failsafe sensor monitor 52 provides additional protection for the patient by detecting any malfunction of failsafe sensor 50 itself. Upon detection of a malfunction, after a delay of a few seconds, failsafe sensor monitor 52 signals logic circuit 30 to override failsafe sensor 50 and to deactivate the system. Simultaneously, message circuit 54 transmits a malfunction message to the LED digital display panel 24, activated by either the failsafe sensor 50 or the failsafe sensor monitor 52. Any malfunction of the device, therefore, results in deactivation of the UV lamps 14, and the microprocessor 16 transmits both audio and video warnings through solid state alarm 44 and service LED 28, respectively.

Figure 8:
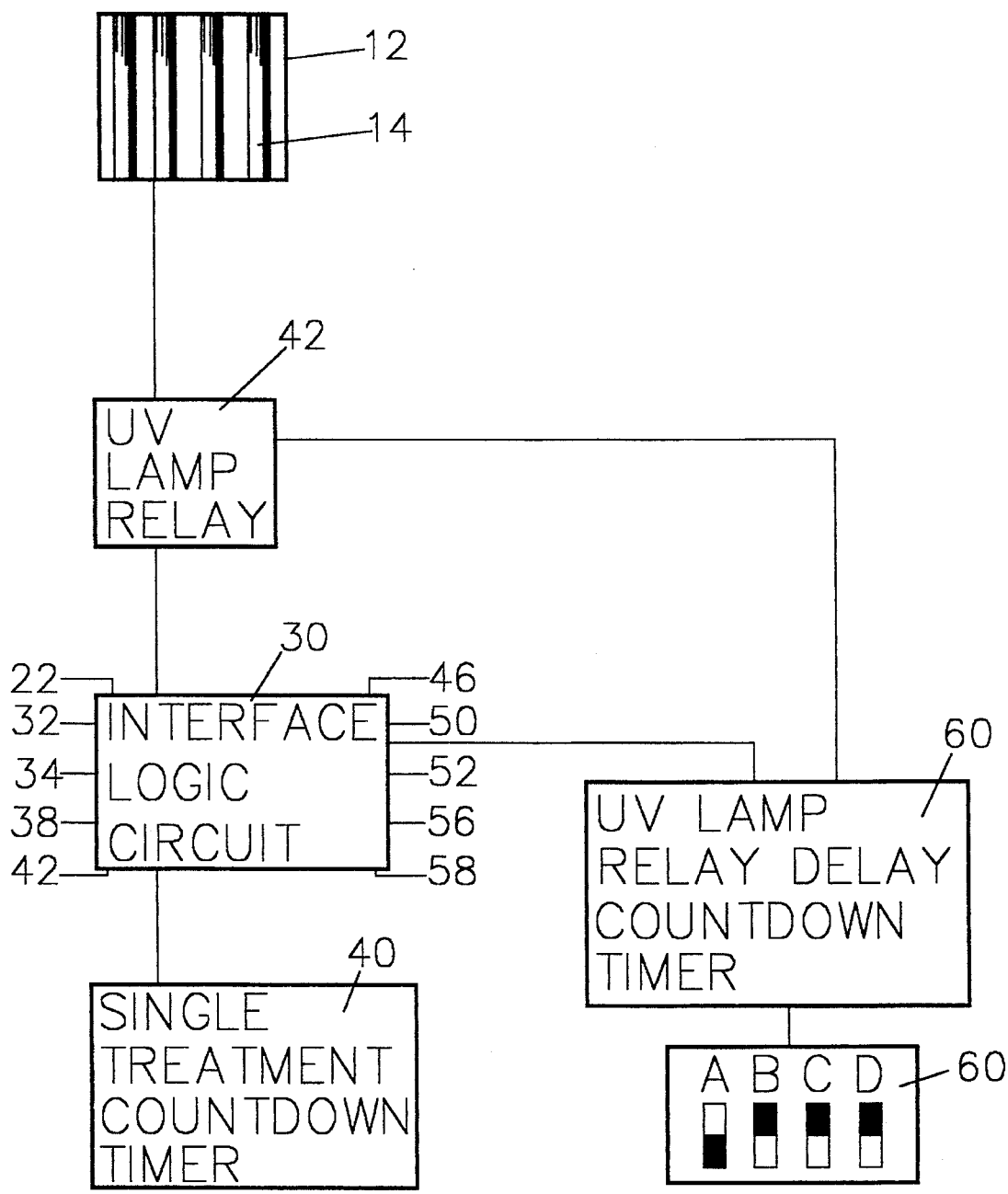
FIG. 8 is a partial schematic block diagram of a modified version of the block diagram of FIG. 7.

In UV phototherapy treatment, it is important that the patient not only faithfully adhere to the prescribed length of each treatment and not exceed the number of treatments prescribed, but also that he limit the number of treatments dispensed by the device within a given length of time. Accordingly, a modified embodiment of the invention provides means to limit the number of treatments that can be dispensed by the inventive device within a predetermined period. This modified embodiment includes the circuitry of FIG. 7, to which the circuitry of FIG. 8 has been added. Thus, as previously described, the single treatment countdown timer 40, FIG. 8, through interface logic circuit 30, opens UV lamp relay 42 after the prescribed treatment time has expired. When UV lamp relay 42 opens, UV lamps 14 are deenergized. Simultaneously with the opening of UV lamp relay 42, single treatment countdown timer 40 activates UV lamp relay delay countdown timer 60 to prevent UV lamp relay 42 from closing until delay timer 60 counts down for a predetermined period of time. For instance, if the physician prescribes one daily treatment, delay timer 60 prevents relay 42 from closing for twenty-four hours. One means of changing the length of the countdown period is a dip switch 62, similar to dip switch 34, which can be selectively preset to establish countdown periods, such as six, twelve, eighteen, or twenty-four hours, with switches 60A, 60B, 60C, and 60D. Other means of reprogramming the timer 60, well known to those skilled in the art, may also be used.

The first embodiment of the subject inventive device is a safe source of ultraviolet phototherapy which protects the patient from inadvertent overdosage of prescribed treatments of ultraviolet radiation, UVA, PUVA, or UVB, by novel means for restricting the length and number of treatments; which permits the patient to receive UV treatments at home; and which provides the physician with means to prescribe home treatment while maintaining reasonable control over the treatments.

It will be appreciated that the ultraviolet ray-dispensing apparatus portion of the invention may take many forms. The apparatus may be a flat rectangular panel, waist high or full body length, which houses several fluorescent tubes. The tubes may be UVA, UVB, or a combination of both. The apparatus may comprise a full enclosure cabinet which completely surrounds the patient with fluorescent ultraviolet tubes. Another embodiment is a compact box-like device into which a hand or foot can be placed for treatment. Yet another embodiment is a small hand-held, wand type, device to be used for treating localized skin problems on various parts of the body. In short, the invention is not limited to any UV specification or to any particular configuration or size of ultraviolet-ray dispensing means.

Other Therapeutic and Diagnostic Machines

There are many embodiments of medical therapeutic and diagnostic devices that rely on timers and periodic calibration, such as X-ray machines, including computed tomography devices ("Cat-scans") and fluoroscopic devices. The energy dispensed by X-ray machines is measured in terms of milliamperes/seconds (MAS) at a predetermined voltage measured in kilovolts. Other diagnostic devices expose patients to electromagnetic energy, such as magnetic resonance imaging machines, which pulse the patient with energy at radio frequencies, and ultrasound devices, which transduce electric pulses into sound pulses, then back to electric pulses. With each of these devices the invention is well suited to provide control means to protect both the patient and the machine in the event of a malfunction.

Figure 9:
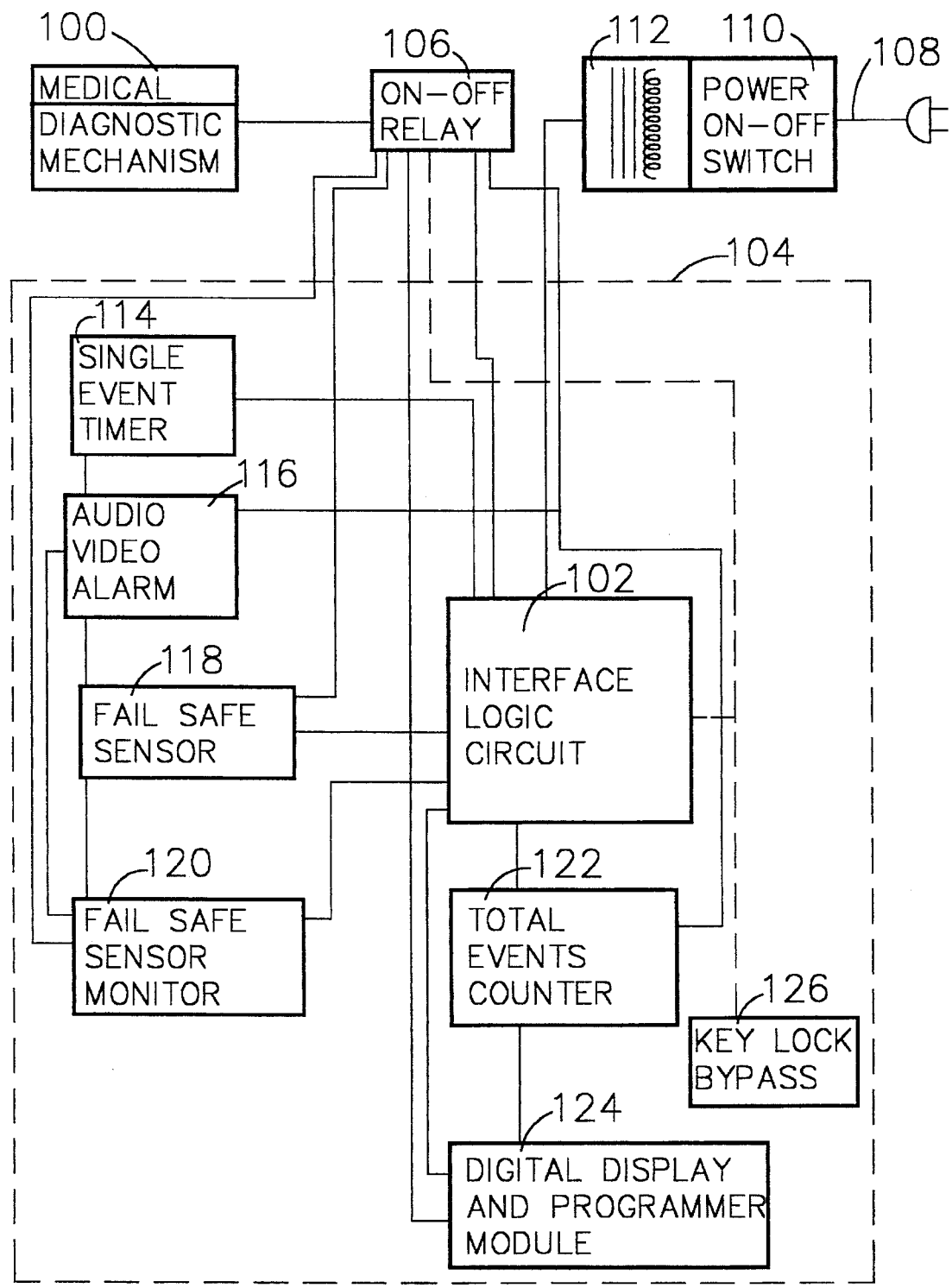
FIG. 9 is a schematic block diagram of another preferred embodiment of the invention.

Referring to FIG. 9, a medical therapeutic or diagnostic mechanism 100 is connected to the interface logic circuit 102 of the microprocessor 104 through an on/off relay 106. A requisite source of power 108 is supplied to the interface logic circuit 102 through power on/off switch 110 and stepdown transformer 112. A single event timer 114 is interconnected between a combined audio/video alarm 116 and interface logic circuit 102. If a malfunction occurs in the single event timer 114, failsafe sensor 118 detects the malfunction and transmits a signal to the interface logic circuit 102, the audio/video alarm 116, and on-off relay 106. Failsafe sensor 118 also monitors the functioning of interface logic circuit 102. In the event of any malfunction, failsafe sensor 118 will cause on/off relay 106 to open. In tandem with failsafe sensor 118 is a failsafe sensor monitor 120 which monitors the functions of the failsafe sensor 118. If failsafe sensor monitor 120 detects a malfunction, it bypasses the failsafe sensor 118, opens the on-off relay 106, and actuates the audio/video alarm 116. A total events counter 122 is programmed to open the on-off relay 106 after a predetermined number of events have been counted and to render the on-off relay 106 unable to restart the mechanism 100.

Simultaneously, a digital display and programmer module 124 displays a first coded number. In order to restart the mechanism 100, a second coded number cross-referenced from the first coded number, must be scrolled onto the digital display 124, which renders on-off relay 106 again operable. Microprocessor 104, therefore, assures that the single event timer is working satisfactorily, and, if it is not, promptly shuts down mechanism 100 to protect the patient. In addition, the program will shut down the mechanism after a predetermined number of events for recalibration and/or preventive maintenance. This total-events shutdown protects both the patient and the mechanism. In lieu of the use of a coded number to reactivate the mechanism, a key-lock bypass 126 is an alternative means to reactivate the on-off relay 106 under certain conditions.

Commercial-Industrial Applications

The subject invention has application to protect industrial machinery from failure in the on position, as well as to shut down a mechanism after a predetermined period for preventative maintenance. Various features of the invention may be selectively applied to a given mechanism. Thus, where only preventative maintenance is a concern, the microprocessor 104, FIG. 9, can be modified to eliminate the single event timer circuitry 114. In other circumstances, only the single event timing circuitry 114 may be of interest, wherein the total events counter 122 may be eliminated. Also, in simple applications, the key-lock bypass 126 may be preferable to the digital display and programmer module 124.

It will occur to those skilled in the art, upon reading the foregoing description of the preferred embodiments of the invention, taken in conjunction with a study of the drawings, that certain modifications may be made to the invention without departing from the intent or scope of the invention. It is intended, therefore, that the invention be construed and limited only by the appended claims.

What is claimed is:

1. A coded prescription-controlled phototherapy treatment dispensing device comprising:

First means for generating therapeutic light emissions treatments;

Second means for activation and deactivation of said first means;

Third means for timing the length of each said therapeutic light emission treatments;

Fourth means for limiting said therapeutic light emission treatments to a prescribed number;

Fifth means for generating and displaying a first coded sequence of numerals when said first means has been activated a predetermined number of times;

Sixth means to cross reference said first coded sequence of numerals to a second coded prescription sequence of numerals prescribing a second sequence of treatments;

Seventh means adapted to override said fourth means responsive to a signal;

Eighth means to convert said second coded prescription sequence of numerals into said signal; and Ninth means to relay said signal to said seventh means, whereupon said coded prescription-controlled phototherapy dispenser is programmed to provide a second series of phototherapy treatments.

2. In combination, an ultraviolet radiation dispensing device and a programmable microprocessor having a first microchip memory bank of a first set of coded, numbered, commands; a second microchip memory bank of a second set of coded, numbered, commands; a digital coded number input module; means to energize said device in response to one of said coded number commands from said first microchip memory bank; means to energize said device for a period of time responsive to a timing number entered in said input module; means to disable said device after a predetermined number of times said device has been energized; means to sequentially display a coded number from said second microchip memory bank on said input module; means to cross reference sequentially displayed coded numbers to companion coded numbers in said first microchip memory bank; and means to enter said companion coded numbers in said input module to generate a command by said microprocessor to reenergize said device.

3. A coded prescription phototherapy treatment dispensing device comprising;

light emission means;

a programmable microprocessor programmed to control the functioning of said light emission means, said microprocessor including switch means adapted to close to energize said light emission means and to open to deenergize said light emission means;

first means to limit each energization of said light emission means to a first predetermined period of time;

second means to disable said light emission means after said light emission means has been energized and deenergized a predetermined number of times; and, countdown means to delay for a predetermined period of time the closing of said switch means.

4. The device of claim 3, including means to program said countdown means to provide selective countdown periods.

5. A coded prescription phototherapy treatment dispensing device comprising:

light emission means;

a programmable microprocessor programmed to control the functioning of said light emission means, said microprocessor including switch means adapted to close to energize said light emission means and to open to deenergize said light emission means;

first means to limit each energization of said light emission means to a first predetermined period of time;

second means to disable said light emission means after said light emission means has been energized and deenergized a predetermined number of times;

a first selection of sequentially increasing stored numbers;

a first number storage bank in said microprocessor in which said sequentially increasing numbers are stored;

a digital number display on said microprocessor;

means to display one of said sequentially increasing stored numbers on said digital number display after said light emission means has been energized a predetermined number of times;

a second selection of random numbers;

a second random number storage bank in said microprocessor in which said random numbers are stored;

means to cross reference one of said first selection of sequentially increasing stored numbers to one of said selection of random numbers;

means to enter one of said selection of random numbers on said digital number display; and, means energized by the entering of one of said selection of random numbers on said digital number display to reactivate said light emission means.

6. The device of claim 5, wherein said one of said first selection of sequentially increasing stored numbers is cross referenced to one or more of said selection of random numbers, any one of which, when entered on said digital number display, will activate said means to reactivate said light emission means.

7. A method of operating a coded prescription phototherapy treatment dispensing device, said device having light emission means; a programmable microprocessor programmed to control the functioning of said light emission means, said microprocessor including switch means adapted to close to energize said light emission means and to open to deenergize said light emission means; first means to limit each energization of said light emission means to a first predetermined period of time; and second means to disable said light emission means after said light emission means has been energized and deenergized a predetermined number of times; a treatment countdown timer and number display;

said method including the steps of:
(a) closing said switch means to energize said device;
(b) entering the length of treatment on said countdown timer;
(c) actuating said means to energize said light emission means for a predetermined period of time;
(d) for a first treatment, locating the portion of the body to be treated in the path of the light emitted by the light emission means for said predetermined period of time;
(e) reactivating the device for a second treatment by repeating preceding steps (a), (b), (c), and (d);
(f) continuing the treatments until the device is disabled by said means to disable said light emission means;
(g) observing the number that appears on said countdown treatment timer and number display prior to the disabling of said device;
(h) cross-referencing said number to a table of numbers to determine a treatment reactivation number;
(i) entering said treatment reactivation number on said treatment countdown timer and number display;
(j) entering on said treatment countdown timer and number display the length of treatment;
(k) actuating said means to energize said light emission means; and,
(1) locating the portion of the body to be treated in the path of the light emitted by said light emission means for said predetermined period of time.

* * * * *